United States Patent [19]

Yamamoto et al.

[11] Patent Number: 4,562,193

[45] Date of Patent: Dec. 31, 1985

[54] 4-[2-(DI- OR TRISUBSTITUTEDPHENOXY)ETHYL AMINO]THIENODIPYRIMIDINES AND INSECTICIDAL AND ACARICIDAL COMPOSITION CONTAINING SAID PYRIMIDINES

[75] Inventors: Shinjiro Yamamoto; Shinji Yokoi; Keigo Matsumoto, all of Shiga; Takeo Honda; Takashi Kobayashi, both of Ube, all of Japan

[73] Assignees: Sankyo Company Limited, Tokyo; UBE Industries Ltd., Ube, both of Japan

[21] Appl. No.: 512,144

[22] Filed: Jul. 8, 1983

[30] Foreign Application Priority Data

Jul. 21, 1982 [JP] Japan .................... 57-127225

[51] Int. Cl.$^4$ .................. C07D 495/04; A61K 31/505
[52] U.S. Cl. ..................... 514/358; 544/278
[58] Field of Search ................ 544/278; 424/251

[56] References Cited

U.S. PATENT DOCUMENTS 4,196,207 4/1980 Webber .................. 544/278

FOREIGN PATENT DOCUMENTS 2043061 10/1980 United Kingdom ........... 544/278

Primary Examiner—George F. Lesmes
Assistant Examiner—S. A. Gibson
Attorney, Agent, or Firm—Frishauf, Holtz, Goodman & Woodward

[57] ABSTRACT

Compounds of formula (I):

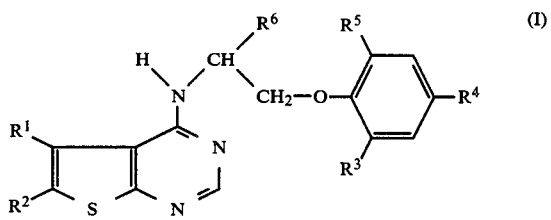

(in which $R^1$, $R^2$ and $R^6$ represent hydrogen or methyl, $R^3$ represents methyl or ethyl, $R^4$ represents an alkyl group or allyl and $R^5$ represents hydrogen, methyl or chlorine) and acid addition salts thereof have acaricidal and insecticidal activity and may be formulated with suitable carriers or diluents for agricultural, horticultural or domestic use. Processes for the preparation of these compounds are also disclosed.

39 Claims, No Drawings

4-[2-(DI- OR TRISUBSTITUTEDPHENOXY)ETHYL AMINO]THIENODIPYRIMIDINES AND INSECTICIDAL AND ACARICIDAL COMPOSITION CONTAINING SAID PYRIMIDINES

BACKGROUND TO THE INVENTION

The present invention relates to a series of new thienopyrimidine derivatives which have valuable insecticidal and acaricidal activities and also provides processes for preparing these derivatives and compositions containing them as the active ingredient.

Insects and acarids cause considerable damage to plants and can represent a serious danger to health; at best, they are a major nuisance. Accordingly, large sums are spent to destroy or deter them. Although many insecticides and acaricides are available, a large number of these have to be used with care, because they can endanger animals or because of their phytotoxicity. Moreover, because insects and acarids have short life cycles, they can develop immunity to many of the commonly used insecticides and acaricides, and accordingly, there is always a continuing need for new compounds exhibiting insecticidal and acaricidal properties.

A series of thienopyrimidine derivatives, which are said to have a variety of biological activities, including fungicidal, bactericidal, anti-viral, insecticidal, acaricidal and plant growth regulatory activities, is disclosed in British patent specification No. 2,043,061. These compounds may be represented by the formula:

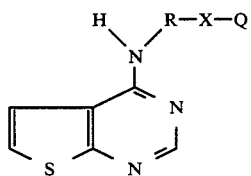

in which R represents an alkylene group optionally having a hydroxy substituent; Q represents a hydrogen atom, a phenyl group, a cycloalkyl group or an alkyl group optionally having one or more halogen, alkoxy or alkoxyalkoxy substituents; and X represents an oxygen or sulphur atom or a sulphonyl group. However, the biological activities of these compounds are not sufficiently high for them to be of practical, commercial use.

We have now discovered that a limited class of compounds similar to certain of those described in U.K. patent specification No. 2,043,061 has substantially more potent insecticidal and acaricidal activities than do the prior compounds and that the compounds, in addition to having such activity against insects and acarids of agricultural importance, are also effective against a variety of domestic insect pests, including flies, such as the housefly or mosquito.

BRIEF SUMMARY OF INVENTION

The compounds of the invention are those thienopyrimidine derivatives of formula (I):

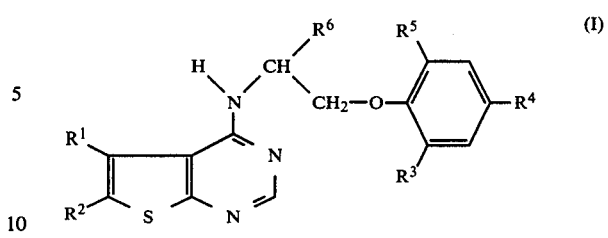

(in which:
$R^1$, $R^2$ and $R^6$ are the same or different and each represents a hydrogen atom or a methyl group;
$R^3$ represents a methyl group or an ethyl group;
$R^4$ represents an alkyl group or an allyl group; and
$R^5$ represents a hydrogen atom, a methyl group or a chlorine atom)
and acid addition salts thereof.

The invention also provides an insecticidal and acaricidal composition comprising, as the active agent, at least one of the compounds of the invention in admixture with a carrier or diluent.

DETAILED DESCRIPTION OF INVENTION

Of the compounds of the invention, we prefer those in which: either $R^1$ and $R^2$ are the same and each represents a hydrogen atom or a methyl group; or $R^1$ represents a methyl group and $R^2$ represents a hydrogen atom. More preferably, $R^2$ represents a hydrogen atom, $R^1$ representing either a hydrogen atom or a methyl group.

$R^6$, which may represent a hydrogen atom or a methyl group, preferably represents a hydrogen atom. $R^5$, which may represent a hydrogen atom, a methyl group or a chlorine atom, likewise preferably represents a hydrogen atom.

Preferred substituents on the phenyl group of the compounds of the invention, that is to say $R^3$, $R^4$ and $R^5$ are as follows:
$R^3$ represents a methyl group;
$R^4$ represents a straight chain alkyl group having from 3 to 7 carbon atoms or an allyl group; and
$R^5$ represents a hydrogen atom. Particularly preferred compounds are those in which $R^3$, $R^4$ and $R^5$ have these preferred definitions, whilst $R^1$ represents a hydrogen atom or a methyl group and $R^2$ and $R^6$ both represent hydrogen atoms.

Examples of alkyl groups which may be represented by $R^4$ in the compounds of the invention include the methyl, ethyl, propyl, isopropyl, butyl, t-butyl, pentyl, isopentyl, hexyl, heptyl, octyl and 2-ethylhexyl groups; however, as noted above, the straight chain groups having from 3 to 7 carbon atoms, that is to say the propyl, butyl, pentyl, hexyl and heptyl groups, are preferred.

The present invention also provides acid addition salts of compounds of formula (I). There is no particular limitation on the acids employed to form such salts, provided that the acids have no adverse effect upon the materials (e.g. plants or agricultural land) to be treated by the compounds of the invention and that the acids do not destabilize the compounds. Suitable acids include: inorganic acids, such as hydrochloric acid, hydrobromic acid, nitric acid or phosphoric acid; carboxylic acids, such as formic acid, oxalic acid or trichloroacetic acid; and organic sulphonic acids, such as methanesulphonic acid or benzenesulphonic acid. Of these acids, hydrochloric acid is preferred.

Examples of preferred compounds of the invention are those compounds listed below; the hydrochlorides of these compounds are also preferred. Where appropriate, the compounds of the invention are hereinafter identified by the numbers appended to them in the following list:

1. 4-[2-(2,4-dimethylphenoxy)ethylamino]thieno[2,3-d]pyrimidine
2. 4-[2-(4-ethyl-2-methylphenoxy)ethylamino]thieno[2,3-d]pyrimidine
3. 4-[2-(2-methyl-4-propylphenoxy)ethylamino]thieno[2,3-d]pyrimidine
4. 4-[2-(4-butyl-2-methylphenoxy)ethylamino]thieno[2,3-d]pyrimidine
5. 4-[2-(2-methyl-4-pentylphenoxy)ethylamino]thieno[2,3-d]pyrimidine
6. 4-[1-methyl-2-(2-methyl-4-pentylphenoxy)ethylamino]thieno[2,3-d]pyrimidine
7. 4-[2-(4-heptyl-2-methylphenoxy)ethylamino]thieno[2,3-d]pyrimidine
8. 4-[2-(4-allyl-2-methylphenoxy)ethylamino]thieno[2,3-d]pyrimidine
9. 4-[2-(2-ethyl-4-methylphenoxy)ethylamino]thieno[2,3-d]pyrimidine
10. 4-[2-(4-butyl-2-ethylphenoxy)ethylamino]thieno[2,3-d]pyrimidine
11. 4-[2-(2-ethyl-4-sec-butylphenoxy)ethylamino]thieno[2,3-d]pyrimidine
12. 4-[2-(2-ethyl-4-pentylphenoxy)ethylamino]thieno[2,3-d]pyrimidine
13. 4-[2-(2,4-dimethylphenoxy)ethylamino]-3-methylthieno[2,3-d]pyrimidine
14. 3-methyl-4-[2-(2-methyl-4-propylphenoxy)ethylamino]thieno[2,3-d]pyrimidine
15. 3-methyl-4-[2-(2-methyl-4-pentylphenoxy)ethylamino]thieno[2,3-d]pyrimidine
16. 4-[2-(2,6-dimethyl-4-propylphenoxy)ethylamino]-3-methylthieno[2,3-d]pyrimidine
17. 4-[2-(4-butyl-2,6-dimethylphenoxy)ethylamino]-3-methylthieno[2,3-d]pyrimidine
18. 4-[2-(2,6-dimethyl-4-pentylphenoxy)ethylamino]-3-methylthieno[2,3-d]pyrimidine
19. 4-[2-(2-chloro-6-methyl-4-propylphenoxy)ethylamino]-3-methylthieno[2,3-d]pyrimidine
20. 4-[2-(4-butyl-2-chloro-6-methylphenoxy)ethylamino]-3-methylthieno[2,3-d]pyrimidine
21. 4-[2-(2-chloro-6-methyl-4-pentylphenoxy)ethylamino]-3-methylthieno[2,3-d]pyrimidine
22. 2,3-dimethyl-4-[2-(2-methyl-4-propylphenoxy)ethylamino]thieno[2,3-d]pyrimidine
23. 2,3-dimethyl-4-[2-(2-methyl-4-pentylphenoxy)ethylamino]thieno[2,3-d]pyrimidine.

The compounds of the invention may be prepared by either of the following Methods.

Method A

A 3-cyano-2-(alkoxymethyleneamino)thiophene (II) is reacted with a 2-(phenoxyalkyl)amine (III), to give an intermediate of formula (IV), which is then rearranged by the addition of a base, to give the desired compound of formula (I), essentially as described in J. Org. Chem. 32, 2376 (1967) and Bull. Soc. Chem. Fr., (1975) 592. The reactions are summarised in the following reaction scheme:

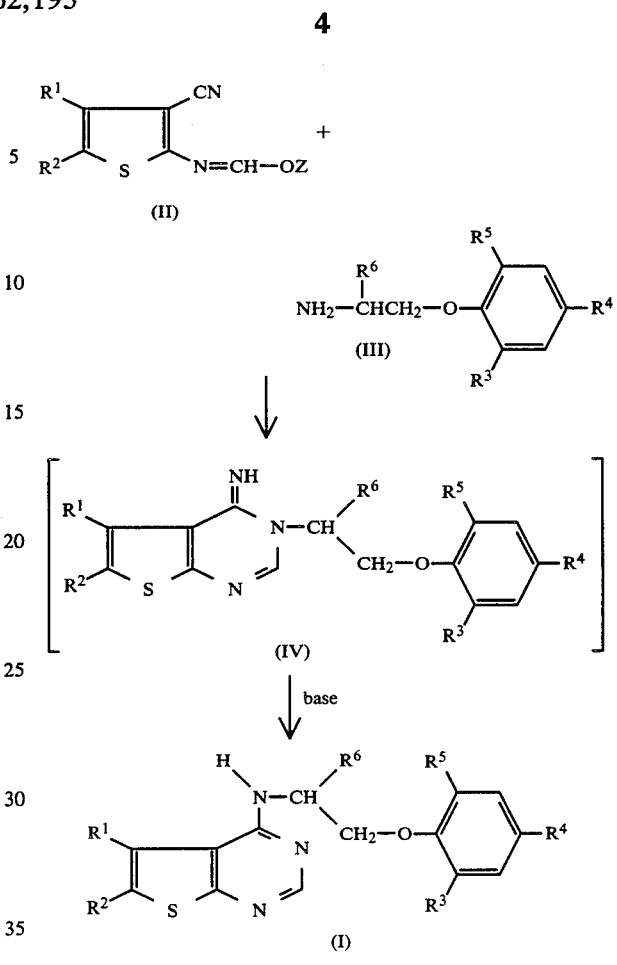

Method B

A 4-halothieno[2,3-d]pyrimidine of formula (V) is reacted with a 2-(phenoxyalkyl)amine of formula (III) in the presence of a base, to give the desired compound of formula (I), as summarised in the following reaction scheme:

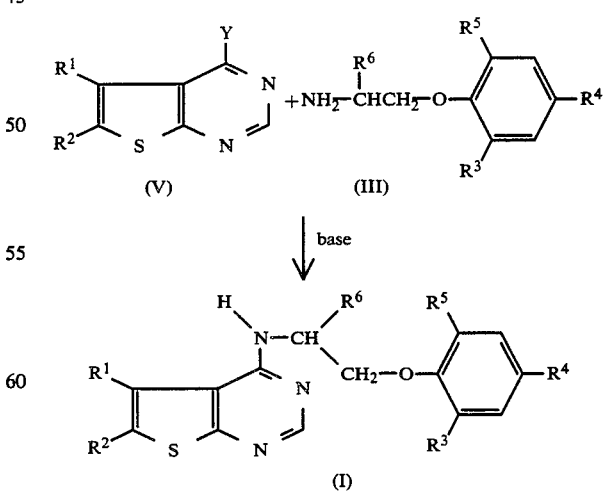

In the above formulae, $R^1$, $R^2$, $R^3$, $R^4$, $R^5$ and $R^6$ are as defined above; Y represents a halogen atom, for example a chlorine, bromine or iodine atom, preferably a chlorine atom; and Z represents a $C_1$–$C_4$ alkyl, preferably a $C_1$ or $C_2$ alkyl, more preferably an ethyl, group.

In both Methods, the reactions are preferably effected in the presence of a solvent. There is no particular limitation on the nature of the solvent employed for these reactions, provided that it has no adverse effect upon the reaction. Suitable solvents include: halogenated and non-halogenated aromatic, aliphatic and alicyclic hydrocarbons, such as benzene, toluene, xylene, methylnaphthalene, petroleum ether, ligroin, hexane, chlorobenzene, the dichlorobenzenes, methylene chloride, chloroform, the dichloroethanes, trichloroethylene and cyclohexane; ethers, such as diethyl ether, ethylene glycol dimethyl ether, tetrahydrofuran and dioxane; ketones, such as acetone and methyl ethyl ketone; alcohols, such as methanol, ethanol and ethylene glycol; mixtures of any two or more of these solvents; and mixtures of one or more of these solvents with water.

Also for both Methods, the reaction temperature is not particularly critical, although we prefer to carry out the reaction at a temperature within the range from ambient temperature to the reflux temperature of the solvent employed. In order to reduce the reaction time, preferably the reactions are carried out with heating.

In Method A, the base employed in the second, or rearrangement, step of the reaction scheme is preferably a strong base, particularly a sodium or potassium alkoxide (such as sodium or potassium methoxide or sodium or potassium ethoxide) or sodium hydride. For Method B, a wide variety of bases, both organic and inorganic may be employed; examples include triethylamine, pyridine, N,N-diethylaniline, sodium alkoxides (such as sodium methoxide or sodium ethoxide), potassium alkoxides (such as potassium methoxide or potassium ethoxide), ammonium acetate, sodium acetate, sodium hydroxide, potassium hydroxide, sodium carbonate, potassium carbonate or sodium hydride.

Upon completion of the reaction, the desired compound may be separated from the reaction mixture by conventional means and then, if necessary, further purified by such conventional techniques as recrystallisation and/or the various chromatographic techniques.

Acid addition salts of the compounds of formula (I) may readily be prepared by introducing the appropriate acid into the reaction mixture, prior to distilling off the reaction solvent.

Compounds of the invention have a strong acaricidal activity, for example, against adults and eggs of Tetranychus, Panonychus and rust mites, which are parasitic to fruit trees, vegetables and flowers. Further, they are active against domestic insects, such as cockroaches and house flies; and various harmful insects in agricultural and horticultural areas such as aphids, diamondback moths, the green rice leafhopper and the brown rice leafhopper.

Reflecting the activity of the present compounds, the invention further provides compositions which contain one or more of the compounds of the invention, together with a carrier and optionally other auxiliary agents, if necessary. The present compositions may be formulated as preparations of the type commonly employed for agricultural use or for use against domestic insect pests, for instance as dusts, coarse dusts, microgranules, fine microgranules, wettable powders, emulsifiable concentrates, aqueous or oily suspensions, and aerosols.

The carrier employed may be natural or synthetic and organic or inorganic; it is generally employed to assist the active ingredient to reach the substrate to be treated, and to make it easier to store, transport or handle the active compound.

Suitable solid carriers include:
inorganic substances, such as clays (examples of which are kaolinite, montmorillonite and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes such as carnauba wax and beeswax; or urea.

Examples of suitable liquid carriers include:
paraffinic or naphthenic hydrocarbons, such as kerosene, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o-chlorotoluene; ethers such as dioxane and tetrahydrofuran; ketones, such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, hexanol, ethylene glycol, diethylene glycol, cyclohexanol, and benzyl alcohol; ether alcohols, such as ethylene glycol monoethyl ether, ethylene glycol monophenyl ether, diethylene glycol monoethyl ether and diethylene glycol monobutyl ether; other polar solvents, such as dimethylformamide and dimethyl sulphoxide; and water.

Suitable gaseous carriers include:
air, nitrogen, carbon dioxide and fluorocarbon propellants such as those sold under the Trade Mark "Freon"; they may be mixed in a known manner to give a propellant.

The compositions of the invention may contain one or more surface active agents and/or polymers to improve the properties of the compositions and help them to disperse, emulsify, spread, penetrate and bind or to control disintegration, improve fluidity or impart corrosion resistance to the composition, or to stabilize the active compound. Any of the conventional classes of surface active agent (non-ionic, anionic, cationic or amphoteric) may be employed, but it is preferred to employ non-ionic and/or anionic surface active agents whereby wetting, adhesion and absorption and desired effects may be improved.

Examples of suitable non-ionic surface active agents include:
the polymerization adducts of ethylene oxide with higher alcohols, such as lauryl alcohol, stearyl alcohol and oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or dialkylphosphoric acids, such as stearylphosphoric acid or dilaurylphosphoric acid; the polymerization adducts of ethylene oxide with amines, such as dodecylamine; the polymerization adducts of ethylene oxide with higher fatty amides, such as stearamide; higher fatty acid esters of polyhydric alcohols, such as sorbitan, and the polymerization adducts of ethylene oxide therewith; and the polymerization adducts of ethylene oxide with propylene oxide.

Examples of suitable anionic surface active agents include:

alkyl sulphate salts, such as sodium lauryl sulphate or oleyl sulphate amine salt; alkyl sulphonate salts, such as sodium dioctyl sulphosuccinate or sodium 2-ethylhexenesulphonate; and aryl sulphonate salts, such as sodium isopropylnaphthalenesulphonate, sodium methylenebisnaphthalenesulphonate, sodium ligninsulphonate or sodium dodecylbenzenesulphonate.

Moreover, the compositions of the present invention may be used in combination with high molecular weight compounds or other formulation agents, such as casein, gelatin, albumin, glue, sodium alginate, carboxymethylcellulose, methylcellulose, hydroxyethylcellulose or polyvinyl alcohol, in order to improve the properties and/or to increase the biological effect of the compositions.

The above-mentioned carriers and various auxiliary agents may be used alone or in any desired combination, depending upon the type of preparation, the application and other factors.

For example, dusts may conveniently contain from 1 to 25% by weight of the active compound, the remainder being a solid carrier.

Wettable powders may conveniently contain, for example, from 25 to 90% by weight of the compound, the remainder being a solid carrier and a dispersing and wetting agent, if required, together with a protective colloidal agent, a thixotropic agent and an anti-foaming agent.

Granules may conveniently contain from 1 to 35% by weight of the active compound, a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the active compound and from 5 to 20% by weight of an emulsifying agent, the remainder being a liquid carrier, together with, if required, a corrosion inhibitor.

Oil preparations may conveniently contain from 0.5 to 5% by weight of the active compound, the remainder being a liquid carrier such as kerosene.

Aerosols may conveniently contain from 0.1 to 5% by weight of the active compound and optionally a perfume, the remainder being an oily and/or aqueous carrier, and a propellant such as liquified petroleum gas, a fluorocarbon or carbon dioxide.

The compositions of the invention may be applied, for example, to paddy or other fields before or after emergence of disease in plants or to plants bearing harmful insects and mites; a concentration of from 100 to 1,000 ppm for the active ingredient is usually suitable, especially for application to leaves and stems of plants and to soil, whereby effective control may be attained.

The composition of the invention may conveniently be blended with other insecticides for a broader insecticidal spectrum and, in some case, a synergistic effect may be expected.

Suitable insecticides include:

phosphorus-containing insecticides such as O,O-diethyl O-(2-isopropyl-4-methyl-6-pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-[2-(ethylthio)ethyl]phosphorodithioate, O,O-dimethyl-1-hydroxy-2,2,2-trichloroethylphosphonate, O,O-diethyl-O-(5-phenyl-3-isoxazolyl)phosphorothioate, O,O-dimethyl-O-(3-methyl-4-methylmercaptophenyl)thiophosphate, O-ethyl-O-p-cyanophenyl phenylphosphonothioate, O,O-dimethyl S-(1,2-dicarboethoxyethyl)phosphorodithioate, 2-chloro-1-(2,4,5-trichlorophenyl)vinyldimethyl phosphate, 2-chloro-1-(2,4-dichlorophenyl)-vinyldimethyl phosphate, O,O-dimethyl O-p-cyanophenyl phosphorothioate, 2,2-dichlorovinyldimethylphosphate, ethyl mercaptophenylacetate O,O-dimethyl phosphorodithioate, S-[(6-chloro-2-oxo-3-benzooxazolinyl)methyl]-O,O-diethylphosphorodithioate, 4-methylthiophenyl dipropylphosphate, 2-chloro-1-(2,4-dichlorophenyl)vinyldiethylphosphate, O,O-diethyl O-(3-oxo-2-phenyl-2H-pyridazin-6-yl)phosphorothioate, O,O-dimethyl S-(1-methyl-2-ethylsulphinyl)ethyl phosphorothioate, O,O-dimethyl S-phthalimidomethyl phosphorodithioate, dimethylmethylcarbamoylethylthioethyl thiophosphorothioate, O,O-diethyl S-(N-ethoxycarbonyl-N-methylcarbamoylmethyl)phosphorodithioate, O,O-dimethyl-S-[2-methoxy-1,3,4-thiadiazol-5(4H)-onyl-(4)-methyl]dithiophosphate, 2-methoxy-4H-1,3,2-benzodioxaphosphorin 2-sulphide, O,O-diethyl-O-(3,5,6-trichloro-2-pyridyl)phosphorothioate, O,S-dimethyl-N-acetyl phosphoroamidothioate, O-2,4-dichlorophenyl O-ethyl S-propylphosphorodithioate, O,O-diethyl S-(2-chloro-1-phthalimidoethyl)phosphorodithioate and O-6-ethoxy-2-ethylpyrimidin-4-yl O,O-dimethylphosphorothioate;

carbamate-type insecticides such as 1-naphthyl N-methylcarbamate, S-methyl-N-[methylcarbamoyloxy]thioacetoimidate, 2-sec-butylphenyl-N-methylcarbamate, 2-isopropoxyphenyl-N-methylcarbamate, 1,3-bis(carbamoylthio)-2-(N,N-dimethylamino)propane hydrochloride and 2-dimethylamino-5,6-dimethylpyrimidin-4-yl dimethylcarbamate;

and other insecticides such as nicotine sulphate, milbemycin D, 6-methyl-2,3-quinoxalinedithiocyclic S,S-dithiocarbonate, 2,4-dinitro-6-sec-butylphenyldimethylacrylate, 1,1-bis(p-chlorophenyl)-2,2,2-trichloroethanol, azoxybenzene, di(p-chlorophenyl)cyclopropyl carbinol, isopropyl 4,4'-dichlorobenzilate, ethyl 4,4'-dichlorobenzilate, ethyl O-benzoyl-3-chloro-2,6-dimethoxybenzohydroxymate, isopropyl 4,4'-dibromobenzilate, tricyclohexyltin hydroxide, hexakis(β,β-dimethylphenethyl)distanoxane, 2-(4-t-butylphenoxy)cyclohexylpropinylsulphide, 3-methyl-1,5-bis(2,4-xylyl)-1,3,5-triazapenta-1,4-diene, 2,4,5,4'-tetrachlorodiphenyl sulphone, hexachlorohexahydromethanobenzodioxathiepine oxide, 5-dimethylamino-1,2,3-trithiane hydrogen oxalate and machine oil.

However, the nature of any such additional insecticide is not critical.

The composition of the invention may be blended with fungicides. Suitable fungicides are as follows.

carbamate-type fungicides such as 3,3'-ethylenebis(tetrahydro-4,6-dimethyl-2H-1,3,5-thiadiazine-2-thione, zinc or manganese ethylenebisdithiocarbamate, bis(dimethyldithiocarbamoyl)disulphide, zinc propylenebisdithiocarbamate, methyl 1-(butylcarbamoyl)-2-benzimidazolcarbamate, 1,2-bis(3-methoxycarbonyl-2-thioureido)benzene and bisdimethyldithiocarbamoyl zinc ethylenebisdithiocarbamate;

dicarboximide-type fungicides such as N-trichloromethylthio-4-cyclohexene-1,2-dicarboximide and N-tetrachloroethylthio-4-cyclohexene-1,2-dicarboximide;

oxazine-type fungicides such as 5,6-dihydro-2-methyl-1,4-oxazine-3-carboxanilide-4,4-dioxide;

naphthoquinone-type fungicides such as 2,3-dichloro-1,4-naphthoquinone;

and other fungicides such as 3-hydroxy-5-methylisoxazole, 5-ethoxy-3-trichloromethyl-1,2,4-thiadiazole, 2,4-dichloro-6-(o-chloroanilino)-1,3,5-triazine, 2,3-dicyano-1,4-dithioanthraquinone, copper 8-quinolate, polyoxin, validamycin, tetrachloroisophthalonitrile, 2-(1-methylpropyl)-4,6-dinitrophenol β,β-dimethylacrylate, triphenyltin hydroxide, phytomycin, dinitromethylheptylphenyl crotonate, 5-butyl-2-dimethylamino-6-methylpyrimidin-4-ol, 6-(3,5-dichloro-4-methylphenyl)-3-(2H)pyridazinone, 6-(3-bromophenyl)-3-(2H)pyridazinone, N-(2,6-dimethylphenyl)-N-methoxyacetylalanine methyl ester and bis(8-guanidinooctyl)amine acetate.

The invention is further illustrated by the following Examples, of which Examples 1 to 8 illustrate the preparation of various of the compounds of the invention, Examples 9 to 12 illustrate the preparation of various compositions of the invention and Examples 13 to 16 illustrate the activities of compounds of the invention. In the Examples, all parts and percentages are by weight, unless otherwise specified.

EXAMPLE 1

4-[2-(2-methyl-4-propylphenoxy)ethylamino]-thieno[2,3-d]pyrimidine (Compound No. 3)

4.9 g of 3-cyano-2-ethoxymethyleneaminothiophene and 5.2 g of 2-(2-methyl-4-propylphenoxy)ethylamine were dissolved in 30 ml of ethanol, and the mixture was heated overnight. The solvent was distilled off, giving 5.3 g of crystals. 3.2 g of these crystals were dissolved in 50 ml of ethanol containing 0.065 mole of sodium ethoxide, and the solution was heated for 6.5 hours, with stirring. It was then cooled and water was added. The oily layer was separated and extracted with benzene. The benzene extract was washed with water and then dried over anhydrous sodium sulphate, after which the solvent was distilled off and the residue was purified by column chromatography through silica gel eluted with a 9:1 by volume mixture of benzene and ethyl acetate, to give 3.2 g of the desired Compound No. 3 in the form of colourless crystals melting at 88°–90° C.

EXAMPLE 2

4-[2-(2,4-dimethylphenoxy)ethylamino]thieno[2,3-d]pyrimidine (Compound No. 1)

5.4 g (0.03 mole) of 3-cyano-2-ethoxymethyleneaminothiophene and 5 g (0.03 mole) of 2-(2,4-dimethylphenoxy)ethylamine were dissolved in 30 ml of ethanol, and the solution was heated under reflux for 7 hours, after which the ethanol was distilled off to give 6.0 g of crystals. 4.5 g (0.015 mole) of these crystals were dissolved in 50 ml of ethanol containing 0.06 mole of sodium ethoxide, and then the solution was heated under reflux for 6 hours. At the end of this time, the reaction mixture was allowed to cool and the crystals which separated were collected by filtration. These crystals were then recrystallised from ethanol, to give 3.4 g (yield 75%) of the desired Compound No. 1 in the form of colourless needles melting at 110°–112° C.

Elemental analysis: Calculated for: $C_{16}H_{17}N_3OS$: C, 64.19%; H,5.72%; N,14.04%. Found: C,63.95%; H,5.80%; N,13.90%.

EXAMPLE 3

4-[2-(2,6-dimethyl-4-propylphenoxy)ethylamino]-3-methylthieno[2,3-d]pyrimidine (Compound No. 16)

3.9 g (0.02 mole) of 3-cyano-2-ethoxymethyleneamino-4-methylthiophene and 4.1 g (0.02 mole) of 2-(2,6-dimethyl-4-propylphenoxy)ethylamine were dissolved in 30 ml of ethanol, and the solution was heated under reflux for 5 hours. It was then cooled and 50 ml of ethanol containing 0.05 mole of sodium ethoxide were added; the whole mixture was then heated under reflux for 6 hours. At the end of this time, the ethanol was distilled off and water was added to the residue. The oily phase was separated and extracted with benzene. The benzene extract was washed with water and dried over anhydrous sodium sulphate, after which the solvent was distilled off and the residue was subjected to column chromatography through silica gel eluted with a 9:1 by volume mixture of benzene and ethyl acetate, to give 4.2 g (yield 59%) of the desired Compound No. 16 in the form of colourless crystals melting at 86°–88° C.

Elemental analysis: Calculated for: $C_{20}H_{25}N_3OS$: C, 67.57%; H,7.09%; N,11.82%. Found: C,67.60%; H,7.20%; N,12.00%.

EXAMPLE 4

4-[2-(2-methyl-4-pentylphenoxy)ethylamino]thieno[2,3-d]pyrimidine (Compound No. 5)

3.4 g (0.02 mole) of 4-chlorothieno[2,3-d]pyrimidine, 4.4 g (0.02 mole) of 2-(2-methyl-4-pentylphenoxy)ethylamine and 2 g (0.02 mole) of triethylamine were dissolved in 50 ml of toluene, and the solution was heated under reflux for 4 hours. At the end of this time, water was added to the reaction mixture, and the mixture was then extracted with toluene. The extract was dried over anhydrous sodium sulphate, and the solvent was distilled off, after which the residue was recrystallised from a mixture of toluene and hexane, to give 5.4 g (yield 76%) of the title compound in the form of colourless crystals melting at 93°–95° C.

Elemental analysis: Calculated for: $C_{20}H_{25}N_3OS$: C, 67.57%; H,7.09%; N,11.82%. Found: C,67.80%; H,7.10%; N,11.70%.

EXAMPLE 5

4-[2-(4-allyl-2-methylphenoxy)ethylamino]thieno[2,3-d]pyrimidine (Compound No. 8.)

3.4 g (0.02 mole) of 4-chlorothieno[2,3-d]pyrimidine, 3.8 g (0.02 mole) of 2-(4-allyl-2-methylphenoxy)ethylamine and 2 g (0.02 mole) of triethylamine were dissolved in 50 ml of benzene, and the solution was heated under reflux for 6 hours. At the end of this time, water was added to the reaction mixture, after which it was extracted with benzene. The extract was dried over anhydrous sodium sulphate and the solvent was distilled off, after which the residue was subjected to column chromatography through silica gel, eluted with a 9:1 by volume mixture of benzene and ethyl acetate, to give 5.4 g (yield 83%) of the desired Compound No. 8, in the form of pale yellow crystals melting at 97°–99° C.

Elemental analysis: Calculated for: $C_{18}H_{19}N_3OS$: C, 66.44%; H,5.88%; N,12.91%. Found: C,66.28%; H,5.85%; N,12.84%.

EXAMPLE 6

4-[2-(2-chloro-6-methyl-4-propylphenoxy)ethylamino]-3-methylthieno[2,3-d]pyrimidine (Compound No. 19)

3.7 g (0.02 mole) of 4-chloro-3-methylthieno[2,3-d]pyrimidine, 4.6 g (0.02 mole) of 2-(2-chloro-6-methyl-4-propylphenoxy)ethylamine and 2 g (0.02 mole) of triethylamine were dissolved in 50 ml of benzene, and the solution was heated under reflux for 6 hours. At the end of this time, the solvent was distilled off and the residue was washed with water and dried in air. It was then recrystallised from a mixture of benzene and hexane, to give 4.5 g (yield 60%) of the desired Compound No. 19 in the form of colourless needles melting at 66°–68° C.

Elemental analysis: Calculated for: $C_{19}H_{22}N_3OSCl$: C, 60.71%; H,5.90%; N,11.18%. Found: C,61.00%; H,6.00%; N,11.20%.

EXAMPLE 7

3-methyl-4-[2-(2-methyl-4-pentylphenoxy)ethylamino]-thieno[2,3-d]pyrimidine hydrochloride (hydrochloride of Compound No. 15)

5 g (0.0136 mole) of 3-methyl-4-[2-(2-methyl-4-pentylphenoxy)ethylamino]thieno[2,3-d]pyrimidine (Compound No. 15) were dissolved in 50 ml of ethanol, and 10 ml of concentrated hydrochloric acid were added at room temperature to the solution. The mixture was stirred for 10 minutes, after which the crystals which precipitated were collected by filtration and recrystallised from ethanol, giving 5.4 g (yield 98%) of the title compound in the form of colourless needles melting at 181°–183° C. This compound is identified in the Tables which follow as "15-HCl".

Elemental analysis: Calculated for: $C_{21}H_{28}N_3OSCl$: C, 62.13%; H,6.95%; N,10.35%. Found: C,62.10%; H,7.00%; N,10.40%.

EXAMPLE 8

Other compounds of the invention were prepared following the general procedures either of Method A (e.g. as in Examples 1–3 above) or Method B (e.g. as in Examples 4–6) above. The melting points and yields, by the respective Methods, of the compounds prepared are summarised in the following Table 1.

TABLE 1

| Compound No. | Yield (%) in Method A | Yield (%) in Method B | Melting point (°C.) |
|---|---|---|---|
| 1 | 75 | — | 110–112 |
| 2 | 82 | — | 106–108 |
| 3 | 82 | — | 88–90 |
| 4 | 68 | — | 90–92 |
| 5 | 70 | 76 | 93–95 |
| 6 | 37 | — | 103–105 |
| 7 | 68 | — | 91–93 |
| 8 | 77 | 83 | 97–99 |
| 9 | 56 | — | 100–101 |
| 10 | 57 | — | 85–87 |
| 11 | 58 | — | 48–50 |
| 12 | 70 | — | 63–65 |
| 13 | 83 | — | 102–104 |
| 14 | 98 | — | 55–58 |
| 15 | 76 | — | 47–49 |
| 16 | 59 | — | 86–88 |
| 17 | 55 | — | 80–82 |
| 18 | 50 | — | 59–63 |
| 19 | 63 | 60 | 66–68 |
| 20 | 46 | — | 38–42 |
| 21 | 24 | — | 66–68 |
| 22 | 49 | — | 70–72 |
| 23 | 64 | — | 70–72 |
| 15-HCl | | 98 | 181–183 |

EXAMPLE 9

Dust 5 parts of Compound No. 5, 50 parts of talc and 45 parts of kaolin were uniformly mixed to form a dust.

EXAMPLE 10

Wettable Powder 50 parts of Compound No. 8, 29 parts of clay, 10 parts of diatomaceous earth, 5 parts of white carbon, 3 parts of sodium ligninsulphonate, 2 parts of "Newcol" 1106 (a grade name of Nihon Nyukazai K.K.) and 1 part of polyvinyl alcohol were uniformly mixed in a mixer and then pulverized three times by a hammer mill to give a wettable powder.

EXAMPLE 11

Granules 70 parts of Compound No. 4 were finely pulverized, and 30 parts of clay were added thereto and then mixed in a mixer to form a premix. 10 parts of this premix were uniformly mixed with 60 parts of clay and 30 parts of bentonite in a mixer. The mixture was then kneaded with a suitable amount of water in a kneader, extruded through a screen with holes having a diameter of 0.8 mm and dried in a draught drier at 50° C. The product thus formed was adjusted by a sifter to form granules.

EXAMPLE 12

Emulsifiable Concentrate 20 parts of Compound No. 5 were mixed with 10 parts of "Sorpol" SM-200 (a trade name of Toho Kagahu K.K.) and 70 parts of xylol, and the mixture was thoroughly blended to give an emulsifiable concentrate.

The present invention is further illustrated by the following Application Examples. Wettable powders prepared according to the procedure of Example 10 were used, each containing 50% by weight of the active compound of this invention.

EXAMPLE 13

Activity against the adult two-spotted spider mite

Test suspensions containing 300 ppm of each of the active compounds shown in Table 2 and 0.01% of a spreader were prepared. Leaves of the cowpea (*Vigna sinensis*) bearing adult two-spotted spider mites (*Tetranychus urticae*) were dipped for 10 seconds into each suspension. After air-drying, the leaves were allowed to stand in a room maintained at 25° C. Each test group contained 50 mites on average.

A mortality of 100% after 24 or 72 hours was taken as 4, a 99–80% mortality after 24 or 72 hours was taken as 3, a 79–60% mortality after 24 or 72 hours was taken as 2, a 57–40% mortality was taken as 1 and a 39% or lower mortality was taken as 0.

For comparison, the test was also carried out with two prior art compounds, which are hereinafter identified by the following codes:
A=4-(2-phenoxyethylamino)thieno[2,3-d]pyrimidine
B=4-(1-methyl-2-phenoxyethylamino)thieno-[2,3-d]pyrimidine.

The results are shown in Table 2.

TABLE 2

| Compound No. | Acaricidal effect 24 hr | Acaricidal effect 72 hr | Compound No. | Acaricidal effect 24 hr | Acaricidal effect 72 hr |
|---|---|---|---|---|---|
| 2 | 2 | 4 | 15-HCl | 4 | 4 |
| 3 | 4 | 4 | 16 | 3 | 4 |
| 4 | 4 | 4 | 17 | 3 | 4 |
| 5 | 4 | 4 | 18 | 3 | 4 |
| 6 | 4 | 4 | 19 | 2 | 4 |
| 7 | 4 | 4 | 20 | 3 | 4 |
| 8 | 4 | 4 | 21 | 3 | 4 |
| 9 | 2 | 3 | 22 | 3 | 4 |
| 10 | 3 | 4 | 23 | 3 | 4 |
| 11 | 2 | 4 | A | 0 | 0 |
| 12 | 3 | 4 | B | 0 | 0 |
| 14 | 4 | 4 | | | |
| 15 | 4 | 4 | | | |

EXAMPLE 14

Ovicidal activity against the two-spotted spider mite

Test suspensions containing 300 ppm of each active compound were prepared as in Example 13. Leaves of the cowpea bearing eggs of the two-spotted spider mite were dipped for 10 seconds into each suspension. After air drying, the leaves were allowed to stand in a room maintained at 25° C.

A 100% ovicidal activity after 2 weeks was taken as 4, a 99–80% ovicidal activity after 2 weeks was taken as 3 and a 39% or lower ovicidal activity was taken as 0.

The results are shown in Table 3.

TABLE 3

| Compound No. | Ovicidal effect | Compound No. | Ovicidal effect |
|---|---|---|---|
| 2 | 4 | 15-HCl | 4 |
| 3 | 4 | 16 | 4 |
| 4 | 4 | 17 | 4 |
| 5 | 4 | 18 | 4 |
| 6 | 4 | 19 | 4 |
| 7 | 4 | 20 | 4 |
| 8 | 4 | 21 | 4 |
| 9 | 3 | 22 | 4 |
| 10 | 4 | 23 | 4 |
| 11 | 4 | A | 0 |

TABLE 3-continued

| Compound No. | Ovicidal effect | Compound No. | Ovicidal effect |
|---|---|---|---|
| 12 | 4 | B | 0 |
| 13 | 4 | | |
| 14 | 4 | | |
| 15 | 4 | | |

EXAMPLE 15

Activity against the final instar larvae of the diamondback moth

Radish leaves were dipped for 30 seconds into test suspensions containing 500 ppm of each of the active compounds shown in Table 4. The leaves were then air-dried and each leaf was placed into a plastic cup having a diameter of 8 cm. 10 final instar larvae of the diamondback moth (*Plutella xylosella*) were released into each cup, and the emergence inhibition rate after 120 hours were assessed. The tests were conducted in duplicate or triplicate, and the results are shown in Table 4.

TABLE 4

| Compound No. | Inhibition rate (%) | Compound No. | Inhibition rate (%) |
|---|---|---|---|
| 1 | 70 | 17 | 67 |
| 2 | 67 | 19 | 85 |
| 3 | 80 | 20 | 73 |
| 4 | 87 | 21 | 60 |
| 5 | 85 | A | 0 |
| 6 | 80 | B | 0 |
| 7 | 67 | | |
| 8 | 75 | | |

EXAMPLE 16

Activity against the green peach aphid

Test suspensions containing 100 ppm of each of the active compounds shown in Table 5 were sprayed onto leaves of a cabbage bearing the green peach aphid (*Myzus persicae*) at the rate of 10 ml per leaf. Each leaf was placed by its leafstalk in a 30 ml bottle containing water and the mouth of the bottle was plugged with cotton wool. The bottles were then left in a room maintained at 25° C. After 72 hours, the percentage mortality of the aphids was assessed. The results are shown in Table 5.

TABLE 5

| Compound No. | Mortality (%) | Compound No. | Mortality (%) |
|---|---|---|---|
| 1 | 81 | 16 | 100 |
| 3 | 86 | 17 | 100 |
| 4 | 94 | 19 | 100 |
| 5 | 86 | 20 | 100 |
| 13 | 75 | 21 | 100 |
| 14 | 100 | A | 0 |
| 15 | 100 | B | 0 |
| 15-HCl | 86 | | |

We claim:
1. Compounds of formula (I):

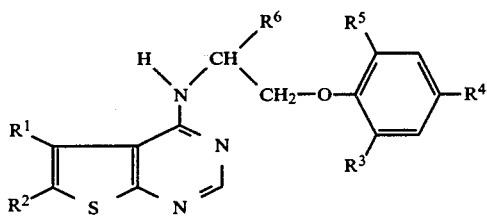

(wherein:
R¹, R² and R⁶ are the same or different and each represents hydrogen or methyl;
R³ represents methyl or ethyl;
R⁴ represents a $C_1$–$C_7$ alkyl group or ally; and
R⁵ represents hydrogen, methyl or chlorine)
and acid addition salts thereof.

2. Compounds as claimed in claim 1, wherein R¹ and R² are the same and each represents hydrogen or methyl.

3. Compounds as claimed in claim 1, wherein R¹ represents methyl and R² represents hydrogen.

4. Compounds as claimed in claim 1, wherein R¹ represents hydrogen or methyl and R² represents hydrogen.

5. Compounds as claimed in claim 1, wherein R⁶ represents hydrogen.

6. Compounds as claimed in claim 1, wherein R⁵ represents hydrogen.

7. Compounds as claimed in claim 1, wherein R³ represents methyl, R⁴ represents a straight chain alkyl group having from 3 to 7 carbon atoms or allyl, and R⁵ represents hydrogen.

8. Compounds as claimed in claim 7, wherein R¹ represents hydrogen or methyl and R² and R⁶ both represent hydrogen.

9. 4-[2-(2,4-Dimethylphenoxy)ethylamino]thieno[2,3-d]pyrimidine of the formula (I) of claim 1.

10. 4-[2-(4-Ethyl-2-methylphenoxy)ethylamino]thieno[2,3-d]pyrimidine of the formula (I) of claim 1.

11. 4-[2-(2-Methyl-4-propylphenoxy)ethylamino]thieno[2,3-d]pyrimidine of the formula (I) of claim 1.

12. 4-[2-(4-Butyl-2-methylphenoxy)ethylamino]thieno[2,3-d]pyrimidine of the formula (I) of claim 1.

13. 4-[2-(2-Methyl-4-pentylphenoxy)ethylamino]thieno[2,3-d]pyrimidine of the formula (I) of claim 1.

14. 4-[1-Methyl-2-(2-methyl-4-pentylphenoxy)ethylamino]thieno[2,3-d]pyrimidine of the formula (I) of claim 1.

15. 4-[2-(4-Heptyl-2-methylphenoxy)ethylamino]thieno[2,3-d]pyrimidine of the formula (I) of claim 1.

16. 4-[2-(4-Allyl-2-methylphenoxy)ethylamino]thieno[2,3-d]pyrimidine of the formula (I) of claim 1.

17. 4-[2-(2-Ethyl-4-methylphenoxy)ethylamino]thieno[2,3-d]pyrimidine of the formula (I) of claim 1.

18. 4-[2-(4-Butyl-2-ethylphenoxy)ethylamino]thieno[2,3-d]pyrimidine of the formula (I) of claim 1.

19. 4-[2-(2-Ethyl-4-sec-butylphenoxy)ethylamino]thieno[2,3-d]pyrimidine of the formula (I) of claim 1.

20. 4-[2-(2-Ethyl-4-pentylphenoxy)ethylamino]thieno[2,3-d]pyrimidine of the formula (I) of claim 1.

21. 4-[2-(2,4-Dimethylphenoxy)ethylamino]-3-methylthieno[2,3-d]pyrimidine of the formula (I) of claim 1.

22. 3-Methyl-4-[2-(2-methyl-4-propylphenoxy)ethylamino]thieno[2,3-d]pyrimidine of the formula (I) of claim 1.

23. 3-Methyl-4-[2-(2-methyl-4-pentylphenoxy)ethylamino]thieno[2,3-d]pyrimidine of the formula (I) of claim 1.

24. 4-[2-(2,6-Dimethyl-4-propylphenoxy)ethylamino]-3-methylthieno[2,3-d]pyrimidine of the formula (I) of claim 1.

25. 4-[2-(4-Butyl-2,6-dimethylphenoxy)ethylamino]-3-methylthieno[2,3-d]pyrimidine of the formula (I) of claim 1.

26. 4-[2-(2,6-Dimethyl-4-pentylphenoxy)ethylamino]-3-methylthieno[2,3-d]pyrimidine of the formula (I) of claim 1.

27. 4-[2-(2-Chloro-6-methyl-4-propylphenoxy)ethylamino]-3-methylthieno[2,3-d]pyrimidine of the formula (I) of claim 1.

28. 4-[2-(4-Butyl-2-chloro-6-methylphenoxy)ethylamino]-3-methylthieno[2,3-d]pyrimidine of the formula (I) of claim 1.

29. 4-[2-(2-Chloro-6-methyl-4-pentylphenoxy)ethylamino]-3-methylthieno[2,3-d]pyrimidine of the formula (I) of claim 1.

30. 2,3-Dimethyl-4-[2-(2-methyl-4-propylphenoxy)ethylamino]thieno[2,3-d]pyridimidine of the formula (I) of claim 1.

31. 2,3-Dimethyl-4-[2-(2-methyl-4-pentylphenoxy)ethylamino)thieno[2,3-d]pyrimidine of the formula (I) of claim 1.

32. An insecticidal and acaricidal composition comprising an active compound in admixture with a carrier or diluent, wherein the active compound is selected from compounds of formula (I):

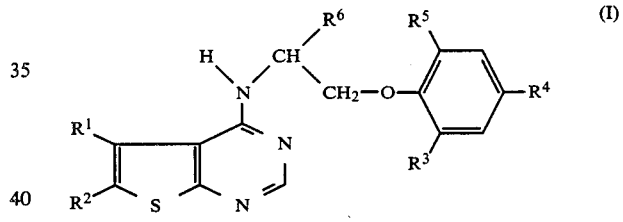

(wherein:
R¹, R² and R⁶ are the same or different and each represents hydrogen or methyl;
R³ represents methyl or ethyl;
R⁴ represents a $C_1$–$C_7$ alkyl group or ally; and
R⁵ represents hydrogen, methyl or chlorine) and acid addition salts thereof.

33. A composition as claimed in claim 32, wherein R¹ and R² are the same and each represents hydrogen or methyl.

34. A composition as claimed in claim 32, wherein R¹ represents methyl and R² represents hydrogen.

35. A composition as claimed in claim 32, wherein R¹ represents hydrogen or methyl and R² represents hydrogen.

36. A composition as claimed in claim 32, wherein R⁶ represents hydrogen.

37. A composition as claimed in claim 32, wherein R⁵ represents hydrogen.

38. A composition as claimed in claim 32, wherein R³ represents methyl, R⁴ represents a straight chain alkyl group having from 3 to 7 carbon atoms or allyl, and R⁵ represents hydrogen.

39. A composition as claimed in claim 38, wherein R¹ represents hydrogen or methyl and R² and R⁶ both represent hydrogen.

* * * * *

UNITED STATES PATENT AND TRADEMARK OFFICE
CERTIFICATE OF CORRECTION

PATENT NO. : 4,562,193

DATED : December 31, 1985

INVENTOR(S) : YAMAMOTO et al

It is certified that error appears in the above-identified patent and that said Letters Patent is hereby corrected as shown below:

Column 12, line 41, change "grade" to --trade--.

Column 15, (Claim 1), line 16, change "ally" to --allyl--.

Column 16, (Claim 30), line 23, change "pyridimidine" to
   --pyrimidine--.

Column 16, (Claim 32), line 46, change "ally" to --allyl--.

Signed and Sealed this

Nineteenth Day of January, 1993

Attest:

DOUGLAS B. COMER

Attesting Officer

Acting Commissioner of Patents and Trademarks